US008858459B2

(12) United States Patent
Chronis

(10) Patent No.: US 8,858,459 B2
(45) Date of Patent: Oct. 14, 2014

(54) OPTICAL MICROSENSOR AND METHODS FOR MONITORING INTRACRANIAL PRESSURE

(75) Inventor: Nikolaos Chronis, Ann Arbor, MI (US)

(73) Assignee: The Regents of The University of Michigan, Ann Arbor, MI (US)

(*) Notice: Subject to any disclaimer, the term of this patent is extended or adjusted under 35 U.S.C. 154(b) by 1402 days.

(21) Appl. No.: 12/577,517

(22) Filed: Oct. 12, 2009

(65) Prior Publication Data

US 2010/0094164 A1    Apr. 15, 2010

Related U.S. Application Data

(60) Provisional application No. 61/104,291, filed on Oct. 10, 2008.

(51) Int. Cl.
*A61B 5/00*    (2006.01)
*G01L 9/00*    (2006.01)
*A61B 5/03*    (2006.01)

(52) U.S. Cl.
CPC ............... *A61B 5/031* (2013.01); *G01L 9/0076* (2013.01); *A61B 2562/0247* (2013.01)
USPC ........................................................ 600/561

(58) Field of Classification Search
CPC .................... A61B 2562/0247; A61B 5/0031; A61B 5/0071; A61B 3/16; G01L 9/002
USPC .................. 600/310, 311, 419, 473, 561, 587
See application file for complete search history.

(56) References Cited

U.S. PATENT DOCUMENTS 4,653,508 A * 3/1987 Cosman ......................... 600/561
4,660,568 A * 4/1987 Cosman ......................... 600/561
5,309,772 A * 5/1994 Hockaday .................. 73/862.59
5,559,358 A * 9/1996 Burns et al. .................... 257/431
5,873,840 A * 2/1999 Neff .............................. 600/561
5,891,184 A   4/1999 Lee et al.

(Continued)

FOREIGN PATENT DOCUMENTS

WO    WO 2007/065140    6/2007

OTHER PUBLICATIONS

Beks, J.W.F et al., "Extradural Transducer for Monitoring Intracranial Pressure," Acta Neurochirurgica, vol. 38, pp. 245-250 (1977).

(Continued)

*Primary Examiner* — Adam Eiseman
(74) *Attorney, Agent, or Firm* — Harness, Dickey & Pierce, P.L.C.

(57) ABSTRACT

A method is provided for internally monitoring pressure of a patient by transmitting an external light source to an implantable microsensor device. The implantable microsensor device has a microlens, a deflectable membrane responsive to a change in pressure of a surrounding environment within the patient, and an array structure disposed between the microlens and the membrane. The array structure includes a first layer that emits a first wavelength of light and a second layer that emits a second wavelength of light responsive to an external light source, where the first and second wavelengths of light are respectively transmissive through the surrounding environment and distinct from one another. Either the array structure or the microlens translates with the membrane in response to the change in pressure of the surrounding environment. The implantable microsensor is compatible with medical imaging devices and does not require an internal or external power supply.

21 Claims, 3 Drawing Sheets

(56) References Cited

U.S. PATENT DOCUMENTS

Figure 1:
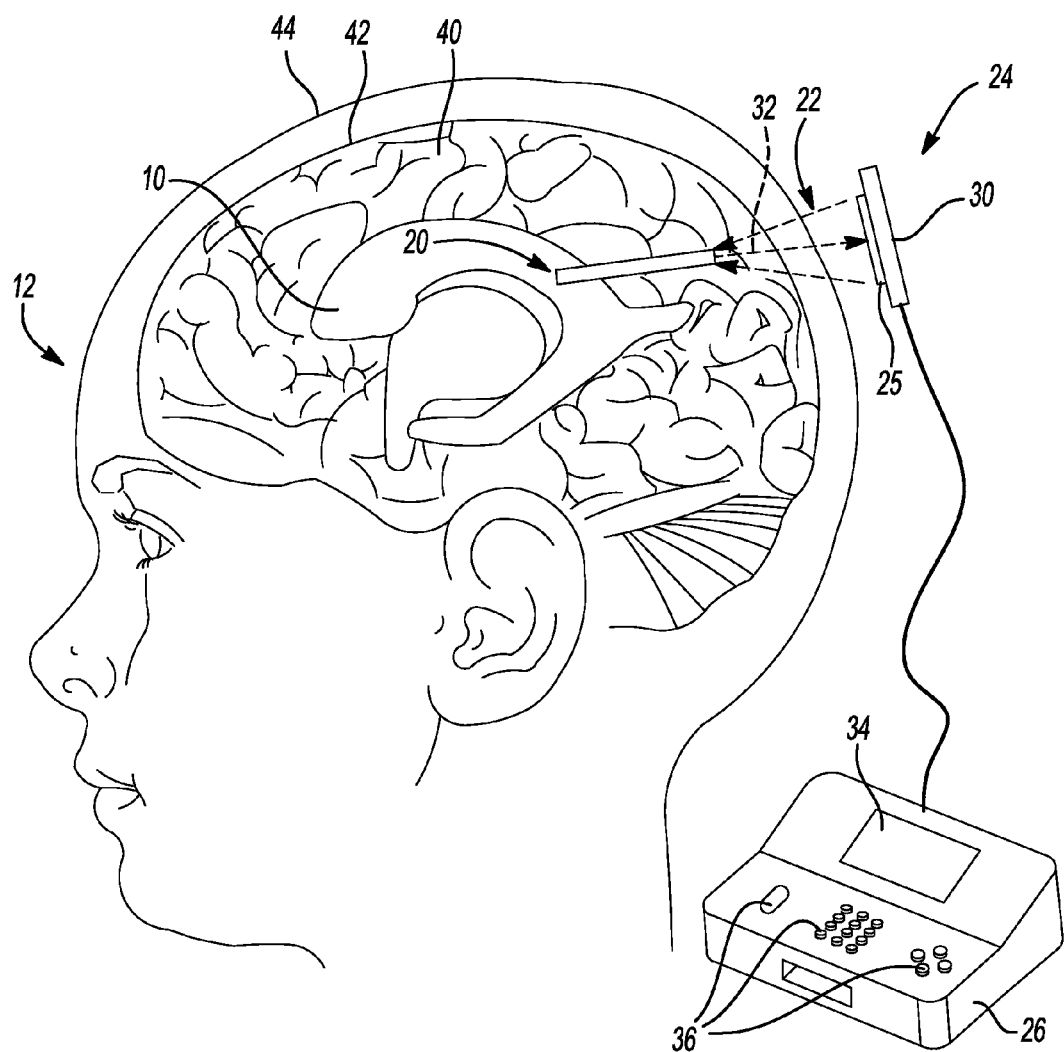

| | | | |
|---|---|---|---|
| 6,111,520 A * | 8/2000 | Allen et al. | 340/870.16 |
| 6,193,656 B1 * | 2/2001 | Jeffries et al. | 600/398 |
| 6,710,355 B2 * | 3/2004 | Youngner | 250/458.1 |
| 2002/0183597 A1 * | 12/2002 | Kaufman et al. | 600/300 |
| 2005/0187488 A1 * | 8/2005 | Wolf | 600/561 |
| 2005/0187509 A1 * | 8/2005 | Wolf | 604/9 |
| 2007/0167867 A1 * | 7/2007 | Wolf | 600/561 |
| 2009/0143696 A1 | 6/2009 | Najafi et al. | |
| 2009/0216149 A1 | 8/2009 | Neff et al. | |

OTHER PUBLICATIONS

Chronis, Nikolas et al., "Tunable liquid-filled microlens array integrated with microfluidic network," Optics Express, vol. 11, No. 19, pp. 2370-2378 (Sep. 22, 2003).

Codman® ICP Monitoring System Quick Set-Up Guide, Codman & Shurtleff, Inc., pp. 1-16 (2001).

de Jong, D.A. et al., "Long-term intracranial pressure monitoring," Medical Progress through Technology, vol. 10, pp. 89-96 (1983/1984).

Firlik, Andrew D. et al, "Intracranial Pressure Monitoring," Neurosurgical Operative Atlas, vol. 5, No. 1, pp. 65-75 (1996).

Flick, Bernd B. et al., "A Portable Microsystem-Based Telemetric Pressure and Temperature Measurement Unit," IEEE Transactions on Biomedical Engineering, vol. 47, No. 1, pp. 12-16 (Jan. 2000).

Jeong, Ki-Hun, et al., "Tunable microdoublet lens array," Optics Express, vol. 12, No. 11, pp. 2494-2500 (May 31, 2004).

Kawoos, U. et al., "A Permanently Implantable Intracranial Pressure Monitor," The Proceedings of the IEEE 31st Annual Northeast Bioengineering Conference, pp. 17-19 (Apr. 2-3, 2005).

Morgalla, M.H. et al., "ICP measurement control: laboratory test of 7 types of intracranial pressure transducers," Journal of Medical Engineering & Technology, vol. 23, No. 4, pp. 144-151 (Jul./Aug. 1999).

Najafi, Nader et al., "Initial Animal Studies of a Wireless, Batteryless, MEMS Implant for Cardiovascular Applications," Biomedical Microdevices, vol. 6, No. 1, pp. 61-65 (2004).

Nulsen, Frank E. et al., "Chronic Intracranial Pressure Monitoring by Telemetry: Clinical Experience," Annals of Biomedical Engineering, vol. 8, pp. 505-513 (1980).

Ostrup, Richard C. et al., "Continuous monitoring of intracranial pressure with a miniaturized fiberoptic device," J. Neurosurg., vol. 67, pp. 206-209 (1987).

The future of fluorescence Qdot® nanocrystal technology, Invitrogen Corporation, pp. 1-15 (2008).

Zhong, Jun et al., "Advances in ICP monitoring techniques," Neurological Research, vol. 25, pp. 339-350 (Jun. 2003).

* cited by examiner

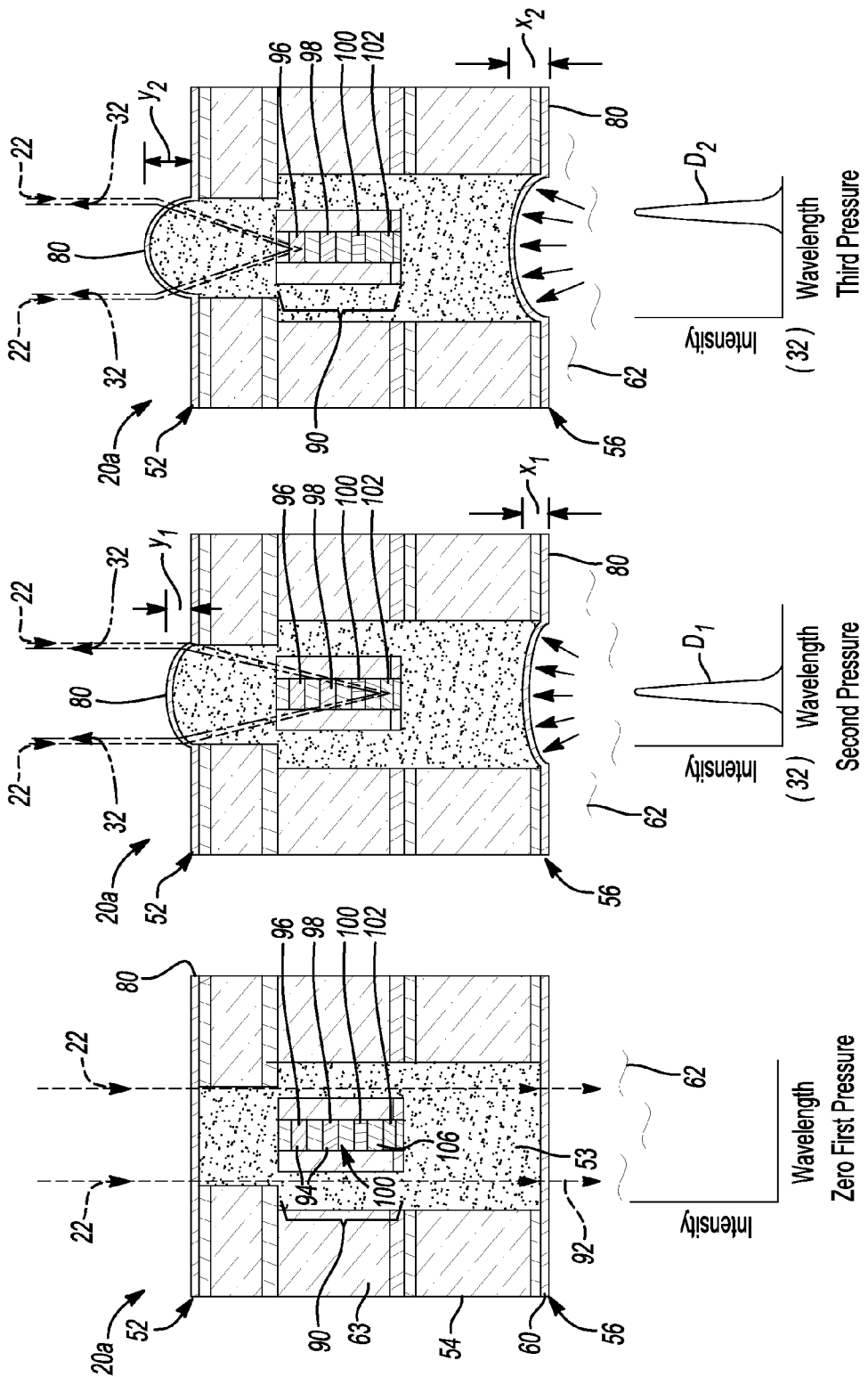

OPTICAL MICROSENSOR AND METHODS FOR MONITORING INTRACRANIAL PRESSURE

GOVERNMENT RIGHTS

This invention was made with government support under NS062313 awarded by the National Institutes of Health. The Government has certain rights in the invention.

CROSS-REFERENCE TO RELATED APPLICATIONS

This application claims the benefit of U.S. Provisional Application No. 61/104,291, filed on Oct. 10, 2008. The entire disclosure of the above application is incorporated herein by reference.

FIELD

The present disclosure relates to intracranial pressure monitoring and, more particularly, relates to an optical microsensor for monitoring intracranial pressure.

BACKGROUND

This section provides background information related to the present disclosure which is not necessarily prior art. Pressure monitoring is an important diagnostic tool for treating various medical conditions, including for example, monitoring of intracranial pressure, ocular pressure, and blood pressure. For example, patients with severe brain injury can suffer from elevated intracranial pressure (ICP). Treatment of such injuries or conditions can be improved by obtaining accurate and readily measured internal pressure within a patient, for example, by implanting a pressure sensor device. It would be desirable to have an implantable sensor device that accurately measures a patient's internal pressure, while reducing risk of infection and enhancing patient safety. Further, such an implanted pressure monitoring sensor would desirably eliminate the need for external or internal power supplies and further would be compatible with medical imaging devices.

SUMMARY

This section provides a general summary of the disclosure, and is not a comprehensive disclosure of its full scope or all of its features.

In various aspects, the present disclosure provides a method for internally monitoring pressure of a patient. In certain aspects, the method comprises transmitting an external light source through tissue of the patient to a microsensor device operable to optically encode internal pressure changes within the patient. In response to receiving the transmitted light, the microsensor device emits light representative of the internal pressure at a near infrared region (NIR) having a wavelength of about 700 nm to about 900 nm. In various aspects, a change in internal pressure relates to a change in a wavelength of emitted light. The method further comprises detecting the emitted light with a spectrometer. In certain aspects, the microsensor device is implanted in an organ selected from the group consisting of: a brain, an eye, and a blood vessel. In certain variations, the microsensor device is also compatible with various medical imaging devices and requires no internal or external power.

In yet other aspects, the present disclosure provides a microsensor device that comprises a microlens and a deflectable membrane responsive to a change in pressure of a surrounding environment within the patient. The microsensor also comprises an array structure, which is disposed between the microlens and the deflectable membrane. The array structure emits light representative of the internal pressure of the surrounding environment at a near infrared region (NIR) having a wavelength of about 700 nm to about 900 nm. The array structure comprises a first layer including a first nanoparticle that emits a first wavelength of light responsive to an external light source and a second layer including a second nanoparticle that emits a second wavelength of light responsive to the external light source. In various aspects, the first wavelength of light and the second wavelength of light are distinct from one another. Either the array structure or the microlens translates with the deflectable membrane in response to the change in pressure of the surrounding environment. In certain variations, the microsensor device is also compatible with various medical imaging devices and requires no internal or external power.

In yet other aspects, the present disclosure pertains to an implantable microsensor for monitoring intracranial or intraocular pressure in a patient. The implantable microsensor comprises a microlens and a deflectable membrane responsive to a change in internal pressure of a brain or an eye of a patient ranging from greater than or equal to about −20 mm Hg to less than or equal to about 300 mm Hg. The microsensor device also comprises an array structure disposed between the microlens and the deflectable membrane. The array structure emits a light representative of the internal intracranial pressure or an intraocular pressure at a near infrared region (NIR) having a wavelength of about 700 nm to about 900 nm. The array structure comprises a first layer including a first nanoparticle that emits a first wavelength of light responsive to an external light source and a second layer including a second nanoparticle that emits a second wavelength of light responsive to the external light source. Either the array structure or the microlens translates with the deflectable membrane in response to a change in pressure of the surrounding brain or eye environment. In certain variations, the microsensor device is also compatible with various medical imaging devices and requires no internal or external power.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2A:
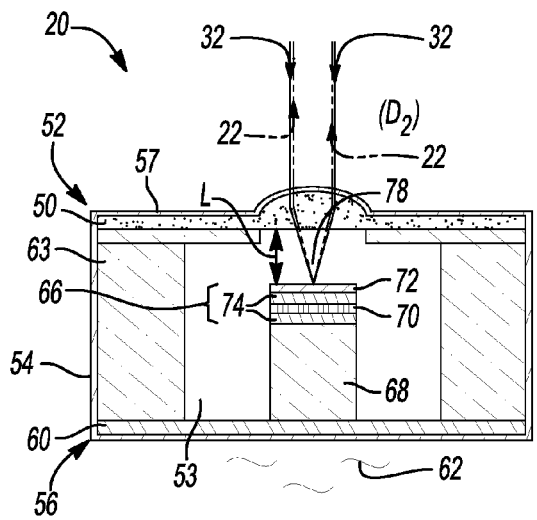
Figure 2B:
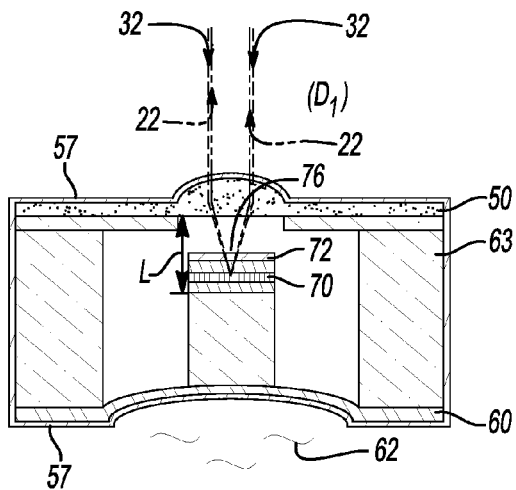
Figure 2C:
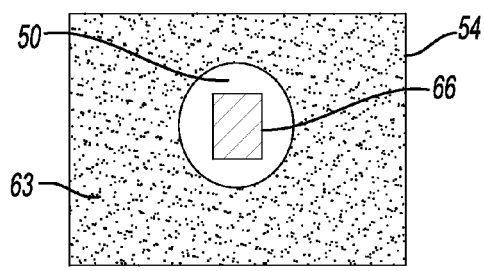

FIG. 1 illustrates operation of a microsensor system in accordance with the principles of the present disclosure having an external light source transmitted through brain tissue of the patient to an implanted microsensor device;

FIGS. 2A-2C show a microsensor device of the present disclosure, where an array structure translates with a deflectable membrane. FIG. 2A depicts a sectional schematic view of the microsensor device where a surrounding environment is at a first predetermined reference pressure. FIG. 2B depicts a sectional schematic view of the microsensor device, where the surrounding environment pressure is increased to a second pressure to translate the deflectable membrane and array structure. FIG. 2C is a plan view of FIG. 2A; and FIGS. 3A-3C show another variation of a microsensor device of the present disclosure having a tunable microlens that translates in response to translation of the deflectable membrane. FIG. 3A depicts a sectional schematic view of the microsensor device where a surrounding environment is at a first predetermined reference pressure, having an inset showing the wavelength of emitted light (which is zero) from the microsensor device. FIG. 3B depicts a sectional schematic view of the microsensor device, where the surrounding environment pressure is at a second pressure that translates the deflectable membrane, which in turn translates the tunable microlens structure, where the inset shows a first wavelength of emitted light ($D_1$) from the microsensor device and array structure representing the second pressure. FIG. 3C depicts a sectional schematic view of the microsensor device, where the surrounding environment pressure is at a third pressure that translates the deflectable membrane, which in turn translates the tunable microlens structure, where the inset shows a second wavelength of emitted light ($D_2$) from the microsensor device and array structure representing the third pressure.

Corresponding reference numerals indicate corresponding parts throughout the several views of the drawings.

DETAILED DESCRIPTION

Exemplary embodiments will now be described more fully with reference to the accompanying drawings. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. Certain terminology is used in the following detailed description for convenience only and is not intended to be limiting. For example, the words "upper" and "lower" are intended to designate direction or orientation shown in the drawings to which reference is being made, but do not necessarily limit the orientation or movement of the components.

Internal pressure monitoring devices in organisms, such as mammals or humans, are important for successful treatment of various conditions, particularly for treatment of certain conditions involving pressure of internal organs or vasculature. For example, conventional intracranial pressure (ICP) monitoring systems are capable of monitoring internal pressure in a brain, but such conventional systems: (a) have a high probability of infection (up to 15%), (b) do not allow long-term ICP monitoring (c) are not MRI (Magnetic Resonance Imaging) compatible and (d) have internal circuitry and/or require internal or external power supply. By way of example, certain conventional ICP monitoring practices employ a catheter that is inserted aseptically through a burr hole into the right ventricle of the brain (intraventricular ICP monitoring). The pressure is measured either by an external fluid-filled transducer that it is connected to the internal catheter, or by a solid-state pressure or a fiber optic transducer that is attached to the tip of the catheter. After the insertion, such catheters are often connected via a cable to the bedside ICP-monitoring system and the pressure is recorded in frequent time intervals (for example, hourly). While such conventional catheter-based systems have been successful in accurately monitoring ICP, they suffer from four major drawbacks: (a) the risk of infection is high, (b) they do not allow long-term ICP monitoring (c) they are not MRI (Magnetic Resonance Imaging) compatible, and (d) they are not passive devices (in that they require introduction of power, current, potential, or impedance, for example, thus often requiring internal circuitry).

Further, successful monitoring of pressure in other organs and tissues, such as pressure in the eye for diagnosis or treatment of diseases like glaucoma, requires a passive pressure monitor having a dimension that is small enough to be minimally invasive to reduce impact on sight and/or to be disposed on a lens type structure. Likewise, in vivo measurement of internal blood pressure within vasculature or other organs requires devices having relatively small dimensions.

Thus, the present disclosure provides a method for internally monitoring pressure of a patient with a microsensor device that accurately measures internal tissue or organ pressure while having relatively small dimensions, being biocompatible, passive, and medical imaging compatible. In various aspects, the implantable microsensors of the present teachings are implanted in an organ or other tissue structure of a patient to monitor internal pressure. In certain variations, the organ is optionally selected from the group consisting of: a brain, an eye, and a blood vessel. The implantable device monitors pressure changes in the patient's organ. Preferably, the implantable microsensor of the present technology detects a change in pressure based on the typical range of pressure for a target organ or tissue. Normal internal tissue pressure ranges depending upon the target organ and animal; however, in humans normal intracranial pressure typically ranges from about 10 mm Hg to about 20 mm Hg, normal eye pressure typically ranges between 0 mm Hg to 80 mm Hg, and normal blood pressure typically ranges between 0 mm Hg to 250 mm Hg. When pressure rises to above about 20 mm Hg in a human, problems potentially arise with the patient's organ, such as those associated with meningitis, encephalitis, Reye's syndrome, diabetic encephalopathy, hepatic encephalopathy, near drowning, hydrocephalus, cerebral infarction, subarachnoid hemorrhage, carotid-cavernous sinus fistula (CCSF), glaucoma, arterial blood pressure, hypertension, congestive heart failure, and the like.

Thus, in certain variations, the implantable microsensors of the present disclosure are capable of detecting a pressure ranging from greater than or equal to about −30 mm Hg to less than or equal to about 300 mm Hg; optionally greater than or equal to about −20 mm Hg to less than or equal to about 275 mm Hg; optionally greater than or equal to about −20 mm Hg to less than or equal to about 250 mm Hg; optionally greater than or equal to about −10 mm Hg to less than or equal to about 150 mm Hg; optionally greater than or equal to about −10 mm Hg to less than or equal to about 100 mm Hg; optionally greater than or equal to about −10 mm Hg to less than or equal to about 90 mm Hg; optionally greater than or equal to about 0 mm Hg to less than or equal to about 80 mm Hg; optionally greater than or equal to about 10 to less than or equal to about 60 mm Hg; or optionally greater than or equal to about 10 to less than or equal to about 20 mm Hg.

In certain aspects, the implantable microsensors are designed to detect a change in pressure of about −10 mm Hg to about 60 mm Hg for applications of monitoring human intracranial pressure. In other aspects, the implantable microsensors are optionally designed to detect a change in pressure of about −20 mm Hg to about 100 mm Hg for human intraocular pressure monitoring. In yet other aspects, the implantable microsensors are designed to detect a change in pressure of about −20 mm Hg to about 300 mm Hg for internal human blood pressure monitoring.

In certain aspects, the implantable microsensor devices are capable of detection of a change of pressure ($\Delta P$) within the surrounding environment (organ or tissue) of ±2 mm Hg; optionally ±1.5 mm Hg; optionally ±1 mm Hg; optionally ±0.75 mm Hg; optionally about ±0.5 mm Hg; optionally ±0.25 mm Hg; and in certain variations, ±0.1 mm Hg.

In certain aspects, the microsensor device is implanted in an organ. In certain variations, the organ is a brain or an eye of a patient. The method comprises transmitting an external light source from outside the patient through tissue of the patient to an internally implanted microsensor device operable to optically encode internal pressure changes within the patient. In certain variations, the microsensor devices of the present disclosure are used to monitor intracranial or intraocular pressure of a patient. Such a method uses a passive device that is wireless and relays accurate pressure information externally without the need of an internal or external power supply, current, impedance, or the like to encode and transmit information. Furthermore, the methods and implantable microsensors of the present disclosure eliminate the need to use an externally connected catheter (such as fluid-filled, solid-state pressure, or fiber optic transducers) or having wires or leads for external connection or coupling with a power source, for example, thus providing a minimally invasive manner and safer manner in which to internally monitor pressure.

As shown in FIG. 1, a brain 10 of patient 12 has an implanted microsensor device 20. For convenience, the description of operational principles of microsensor device 20 is discussed with respect to the brain 10; however, such principles are not limited to the brain and as appreciated by those of skill in the art are applicable to various organs or vasculature within a patient's body to detect internal pressure. After microsensor device 20 has been implanted within the brain tissue 10 at an intraventricular location within brain 10 via conventional catheter-based placement, the microsensor device 20 passively provides information externally regarding internal pressure changes within brain 10. For example, a monitoring system 24 includes a remote light generating unit 25 from which externally generated light energy, referred to herein as external light source 22, can be generated and directed towards microsensor 20.

The monitoring system 24 further includes a portable readout base unit 26 that is connected to the remote light generating unit 25 (which may generate external source of light 22 within the base unit 26 and transmit the light 22 to remote light generating unit 25 for placement near the patient's skull). Monitoring device 24 also includes a spectrometer 30 for receiving emitted light energy from the microsensor device 20. Readout base unit 26 can optionally include a processor (not shown) for receiving information from spectrometer 30 to determine internal pressure within the organ based on light energy 32 emitted from microsensor 20. Further, readout base unit 26 includes a graphical user interface 34, user input and control systems 36 to appropriately operate the readout base system 26, including control and activation of the spectrometer 30 and light generating unit 25 to appropriately monitor pressure via the monitoring system 24. The portable readout unit 26 may be connected during use to an external computer processing unit or may include internal memory, which can later transmit stored data to an external computer processing unit.

External light source 22 is used to stimulate the microsensor device 20 to emit and transmit light (referred to herein as "emitted light" 32) having a wavelength recognized by spectrometer 30. In certain aspects, the external light source 22 is generated by remote light generating unit 25. External light source 22 preferably transmissive through tissue of the patient (here through various layers of tissue, including by way of non-limiting example, brain tissue 10, dura matter 40, skull bone 42, and skin tissue 44, to reach the microsensor device 20, which optically encodes internal pressure changes within the patient's brain 10.

For example, in certain embodiments, external light source 22 of the present disclosure transmits a wavelength in the near infrared (NIR) region of about greater than or equal to about 650 nm to less than or equal to about 850 nm, optionally greater than or equal to about 700 nm to less than or equal to about 800 nm, optionally greater than or equal to about 700 nm to less than or equal to about 750 nm. In certain embodiments, external light source 22 generates an NIR wavelength of about 705 nm. As discussed below and illustrated in FIG. 1, external light source 22 is external to the patient 12 and when stimulation is necessary (for a reading of internal pressure) the external light source 22 is actuated and brought within range of patient 12 to excite materials in the microsensor device 20 to emit wavelengths (32) that represent pressure or pressure changes within the patient's organ in which the microsensor device 20 is implanted. Suitable examples of remote light generating unit 25 that generates external source of light 22, may include a light emitting diode (LED), a laser, a near infrared halogen lamp, and the like.

In response to receiving the transmitted external light source 22 through the brain tissue 10, the microsensor device 20 generates emitted light 32, which is representative of the internal pressure of the patient's brain 10. In various aspects, emitted light 32 is transmissive to the tissue through which it passes to be adequately transmitted external to patient 12 to be received by spectrometer 30. For example, in certain embodiments, wavelengths of emitted light 32 in the NIR region are selected due to the attributes of weak absorption by the tissue. Accordingly, in certain variations, the microsensor device 20 is designed to generate emitted light 32 at a near infrared region (NIR) having a wavelength of greater than or equal to about 700 nm to less than or equal to about 900 nm, optionally greater than or equal to about 705 nm to less than or equal to about 850 nm, optionally greater than or equal to about 710 nm to less than or equal to about 800 nm, optionally greater than or equal to about 715 nm to less than or equal to about 750 nm. For example, designing the monitoring system 24 to employ an NIR range of light maximizes efficient transmission of light energy through the brain, because the absorption coefficient ($\mu_a$) of the brain tissue in the NIR spectrum window is very small ($\mu_a < 0.1$ mm$^{-1}$, Bevilacqua et al., 1999; Kim and Lee, 2005, the relevant portions of which are incorporated herein by reference).

The microsensor device 20 is implanted within the target organ and remains within the organ for long-term monitoring of pressure with minimal risk of infection or risk of interference with imaging devices, such as magnetic resonance imaging (MRI), computed axial tomography (CT), and ultrasound. As previously discussed, the implantable microsensor device 20 is wireless and relays pressure information externally without the need of an internal power supply to perform.

In certain aspects, the microsensor device 20 used to internally monitor pressure of a patient 12 is as shown in FIGS. 2A-2C. The implantable microsensor 20 can be implanted through surgical procedures known in the art. The microsensor device 20 comprises a microlens 50 on a first side 52 of a housing 54. A second diametrically opposite side 56 of the housing 54 includes a deflectable membrane 60, which is responsive to any changes in pressure of a surrounding environment 62 within the patient 12. The housing 54 further includes walls 63, which extend from first side 52 to second side 56 to enclose the microsensor device 20 to prevent any fluid communication with the external surrounding environment 62.

The surface of the housing 54 comes in contact with tissue within a patient's body and is preferably formed of, treated to be, or coated with biocompatible materials. Suitable biocompatible materials for the housing include polymers, silicone, polytetrafluoroethylene (commercially available under the trade name TEFLON® sold by E.I. Du Pont de Nemours), polyetheretherketone (PEEK) polymer, polycarbonates, polymethylmethacrylate (PMMA), combinations thereof, as well as other biocompatible materials and/or biodegradable materials known in the art. In certain embodiments, a coating 57 may be applied to exterior walls 63 for maintaining biocompatibility and integrity of the housing 54. In certain variations, a coating thickness optionally ranges from about 0.1 μm to about 2 μm. Coating 57 can protect the microstructure device 20 and its internal components from the patient's immune system and facilitate long-term indwelling via implantation. Suitable examples of coating 57 materials include polymers, silicone, polytetrafluoroethylene (TEFLON®), polyetheretherketone (PEEK) polymer, polyxylylene or its derivatives (parylene), combinations thereof, as well as other biocompatible materials and/or biodegradable materials known in the art. In certain aspects, the coating 57 material is polyxylylene or its derivates (parylene). It should be appreciated that coating 57 may include different materials and may have a different composition in certain regions of housing 54 (e.g., to enhance adhesion to different underlying material compositions).

The housing 54 optionally further comprises a fluid 53 that is transmissive to external light source 22 (and emitted light 32, which will be described in more detail below). Housing 54 can be filled with any fluid 53 having an index of refraction that is equal to or higher than that of the microlens 50. Examples of suitable types of fluid 53 include gas, liquid, and semi-liquid. Specifically, suitable examples include air, water, polydimethylsiloxane (PDMS), hydraulic gel, polymer-based compositions, biocompatible materials, biodegradable materials and the like. In certain, aspects, housing 54 is filled with air.

The housing 54 of microsensor device 20 is sized according to the size of the patient's organ in which it is to be implanted. The present disclosure contemplates using microsensor devices 20 independently implanted or introduced within target tissue or a target organ of a patient or alternately being used in conjunction with or coupled to medical devices or other types of medical implants, known to those of skill in the art, which are introduced and/or implanted internally in the patient. For example, to monitor intracranial pressure the device is independently implanted through a burr hole in the skull of 42 the patient. By way of another example, to monitor pressure in the eye the device is optionally coupled to or integrated into a silicon-based intraocular lens. For monitoring blood pressure, the microsensor device may be independently introduced to vasculature (or may move within the circulatory system) or be incorporated into a stent or other heart or vascular implant.

In various aspects, the dimensions of housing 54 are of a relatively small scale, for example, on a microscale. Thus, in certain aspects, microsensor device's 20 housing 54 has at least one major dimension that is less than or equal to about 15 mm, optionally less than or equal to about 10 mm, optionally less than or equal to about 6 mm, optionally less than or equal to about 5 mm, optionally less than or equal to about 3 mm, optionally less than or equal to about 2 mm, optionally less than or equal to about 1 mm, optionally less than or equal to about 0.9 mm (900 μm), optionally less than or equal to about 0.8 mm (800 μm), optionally less than or equal to about 0.7 mm (700 μm), optionally less than or equal to about 0.6 mm (600 μm), less than or equal to about 0.5 mm (500 μm), optionally less than or equal to about 0.1 mm (100 μm), optionally less than or equal to about 75 μm, optionally less than or equal to about 50 μm, optionally less than or equal to about 40 μm, optionally less than or equal to about 30 μm, optionally less than or equal to about 25 μm, and in certain aspects, optionally less than or equal to about 20 μm. In certain aspects, microsensor device's 20 housing 54 has at least one major dimension (e.g., length) that is less than or equal to about 10 mm for implantation into a human patient's brain for intracranial pressure monitoring. In other aspects, microsensor device's 20 housing 54 has at least one major dimension (e.g., length) that is less than or equal to about 1 mm for implantation into a human patient's eye for intraocular pressure monitoring.

In certain aspects, housing 54 is sized such that all dimensions are is less than or equal to about 5 mm, optionally less than or equal to about 3 mm, optionally less than or equal to about 2 mm, optionally less than or equal to about 1 mm, optionally less than or equal to about 0.9 mm (900 μm), optionally less than or equal to about 0.8 mm (800 μm), optionally less than or equal to about 0.7 mm (700 μm), optionally less than or equal to about 0.6 mm (600 μm), less than or equal to about 0.5 mm (500 μm), optionally less than or equal to about 0.1 mm (100 μm), optionally less than or equal to about 75 μm, optionally less than or equal to about 50 μm, optionally less than or equal to about 40 μm, optionally less than or equal to about 30 μm, optionally less than or equal to about 25 μm, and in certain aspects, optionally less than or equal to about 20 μm. In certain aspects, the housing 54 dimensions of microsensor device 20 range from greater than or equal to about 25 μm to less than or equal to about 3 mm; optionally greater than or equal to about 30 μm to less than or equal to about 2 mm, optionally greater than or equal to about 30 μm to less than or equal to about 1 mm. Such embodiments are particularly suitable for use in a patient's eyes to minimize obstruction of eyesight or within vasculature potentially having smaller diameters.

In yet other aspects, housing 54 is sized such that at least one major dimension (e.g., length) is less than or equal to about 10 mm, while width is less than or equal to about 3 mm. In certain aspects, the housing 54 dimensions of microsensor device 20 range from greater than or equal to about 25 μm to less than or equal to about 3 mm; optionally greater than or equal to about 30 μm to less than or equal to about 1 mm.

The deflectable membrane 60 is responsive to pressure changes in an external surrounding environment (e.g., 62). By way of example, deflectable membrane 60 is responsive to changes in intracranial pressure, ocular pressure, blood vessel pressure and the like. Thus, at least a portion of deflectable membrane 60 is formed of a flexible or elastomeric material that is capable of deflection in response to pressure changes in the tissue of the surrounding environment 62. In FIG. 2A, deflectable membrane 60 is in a non-deflected state, where a pressure of surrounding environment 62 is at a predetermined steady state level and the deflectable membrane 60 is relatively flat.

Upon an increase in pressure of surrounding environment 62 as shown in FIG. 2B, deflectable membrane 62 translates in a direction toward first end 52 of housing 54 by upward deflection. As appreciated by those of skill in the art, while not shown, the translation or movement of deflectable membrane 60 may also be in the opposite direction if pressure falls in the surrounding environment 62. Examples of suitable materials for deflectable membrane 60 include polymers like polydimethylsiloxane (PDMS), poly-paraxylylene (Parylene), silicone, hydrogels, nitrides, oxides, carbides, silicides, as well as other biocompatible materials and/or biodegradable materials known in the art. As shown in FIGS. 2A and 2B, coating 57 optionally overlies the deflectable membrane 60. As noted above, suitable examples of coating materials include polymers, silicone, polytetrafluoroethylene (TEFLON®), polyetheretherketone (PEEK) polymer, polyxylylene or its derivatives (parylene), biocompatible materials, biodegradable materials and the like. In certain aspects, the deflectable membrane 60 is formed of PMDS and is overlaid with coating 57 of parylene.

An array structure 66 is disposed within housing 54 located between microlens 50 and deflectable membrane 60. As seen in FIGS. 2A-2C, the array structure 66 is disposed in transmissive fluid 53. The array structure 66 receives external light source 22 which is transmitted through microlens 50. The array structure 66 is located in the microlens' 50 focal plane. With either location of the array structure 66, light passes through the microlens 50 and excites a layer within the array structure 66. The array structure 66 then emits light following the path the light 22 entered the microlens 50. When the deflectable membrane 60 is deflected under pressure of an external surrounding 62, the emitted light 32 is representative of this pressure.

In the embodiment of FIGS. 2A-2C, the microlens 50 is fixed and light passing there through travels a distance "L" into the interior of housing 54, which reaches array structure 66 that is located in the microlens' 50 focal plane. In this embodiment, microlens 50 can be formed from a relatively rigid material, such as those selected from the group consisting of: silicon oxides, including silicon dioxide, polysiloxane materials, including polydimethylsiloxane (PDMS), photoresist materials, polycarbonates, acrylic polymers or derivatives thereof, including methacrylates, such as polymethylmethacrylates (PMMA), optical adhesives (such as commercially available ultraviolet curable photopolymer sold by Norland Products as NORDLAND OPTICAL ADHESIVE 61™), and other rigid plastics, including any other rigid biocompatible materials and/or biodegradable materials known in the art. Array structure 66 is coupled to deflectable membrane 60 and thus translates with any movement of deflectable membrane 60. As shown, an optional spacing element 68 is connected to deflectable membrane 60.

Array structure 66 includes a plurality of distinct layers, including at least a first layer 70 and a second layer 72, where the plurality of distinct layers are configured to emit a range of wavelengths. Each distinct layer 70, 72 transmits light through the organ in which microsensor device 20 is implanted at a different wavelength. By way of example, each of the plurality of layers emits a different wavelength, which represents pressure changes. The plurality of distinct layers can be fabricated to emit different wavelengths such as, 700 nm, 740 nm, 780 nm, 820 nm, 860 nm and 900 nm, by way of non-limiting example.

The wavelengths are representative of the pressure level in the organ, which are transmitted to the external spectrometer 30 (FIG. 1). Interstitial spacing layers 74 are disposed beneath each of first and second layers 70, 72. Suitable examples of materials for spacing element 68 or interstitial spacing layer 74 include silicon, silicon dioxide, polydimethylsiloxane (PDMS), polymethylmethacrylate (PMMA), polymers of hydroxy ethyl methacrylate (HEMA) monomer, cellulose, lactone polymers, polystyrene, polyxylylene or its derivatives (parylene), indium oxide (ITO), photoresist materials, optical adhesives (such as commercially available ultraviolet curable photopolymer sold by Norland Products as NORDLAND OPTICAL ADHESIVE 61™), combinations thereof, as well as other biocompatible materials and/or biodegradable materials known in the art. The thickness spacing element 68 or interstitial spacing layer 74 may vary depending on the application. It should be appreciated that while spacing element 68 and interstitial spacing layers 74 are shown, they are merely optional and may be omitted.

As shown in FIGS. 2A-2C, first layer 70 includes a first nanoparticle material (a plurality of first nanoparticles having the same composition that are used within the layer), such as a first quantum dot material, which emits a first wavelength of light $(\lambda_1)$(76) responsive to the external light source 22. Second layer 72 comprises a second nanoparticle that emits a second wavelength of light $(\lambda_2)$(78) responsive to the external light source 22. Second nanoparticle can be a second quantum dot material. In various aspects, first wavelength of light $(\lambda_1)$(76) and the second wavelength of light $(\lambda_2)$(78) are distinct from one another.

As appreciated by those of skill in the art, the array structure 66 may comprise a plurality of layers, in addition to the first and second layers 70, 72, in any configuration or sequence. Additionally, each respective layer may comprise a plurality of materials that emits the same or different wavelengths of light responsive to external light source 22, as well as other conventional components for such layer structures. Such nanoparticles can also be embedded in layers made from polydimethylsiloxane (PDMS), photoresist materials, such as epoxy based SU-8. The respective first wavelength of light $(\lambda_1)$(76) and the second wavelength of light $(\lambda_2)$(78) are emitted when external light source 22 reaches the respective layers 70, 72 and thus generates a combined emitted light 32, which passes through microlens 50 through the surrounding environment 62 for detection (for example, as shown in FIG. 1, brain 10, dura matter 40, skull bone 42, and scalp/skin 44 to spectrometer 30).

Conventional fabrication processes for quantum dot arrays are known and can be used in accordance with the present teachings. Each layer (e.g., first and second layers 70, 72) can be fabricated as a quantum dot array that emits a different wavelength in the near infrared (NIR) region from about 700 nm to about 900 nm. As appreciated by those of skill in the art, such emitted wavelength ranges from nanoparticles often vary in a range for a single nanoparticle, and have a broad spectrum covering multiple wavelengths. Further, such emissions are often dependent upon the excitation wavelength received. However, suitable nanoparticle quantum dots for the present technology are selected for emission in a desirable range (NIR wavelength emissions), when receiving an external light source wavelength of greater than or equal to about 650 nm to less than or equal to about 850 nm. Thus, it should be appreciated that a nanoparticle emitting light at the specified wavelength discussed herein may indeed emit a broader range of wavelengths and is not limited to the wavelength specified, particularly as the external light source 22 wavelength may vary.

Non-limiting examples of nanoparticles for a quantum dot array may emit at 700 nm, 705 nm, 740 nm, 780 nm, 800 nm, 820 nm, 860 nm, or 900 nm. Nanoparticles for each respective layer may independently comprise a nanoparticle compound including an element selected from the group consisting of: cadmium, indium, selenium, tellurium, zinc, sulfur, phosphorus, and combinations thereof. By way of non-limiting example, suitable nanoparticle materials include flourophores, which may include compounds such as cadmium selenide, cadmium sulfide, indium arsenide, indium phosphide, and the like, as well as combinations thereof. Suitable nanoparticle materials are commercially available from Invitrogen under the trade name QDOT® nanocrystals. In certain products, the commercially available QDOT® nanoparticles may comprise a core of a semiconductor material, such as cadmium mixed with selenium or tellurium. A semiconductor shell can be present, such as zinc sulfide, which surrounds and stabilizes the core material. An amphiphilic polymer optionally coats and encases the core-shell nanoparticles, which can be covalently modified with a functionalized polyethylene glycol (PEG) outer coating. As appreciated by those of skill in the art, the quantum dot array may comprise a plurality of distinct nanoparticle materials that combine together to form a tailored wavelength emission.

For example, the first layer 70 can be configured to emit a wavelength at about 705 nm and second layer 72 can be configured to emit a wavelength at about 800 nm. The first layer 70 and the second layer 72 can comprise nanoparticle compositions independently selected from the group consisting of: cadmium selenide, cadmium sulfide, indium arsenide, indium phosphide, and the like. Particularly suitable commercially available nanoparticles for use in quantum dot arrays of layers 70, 72 include those with emissions of 705 nm or 800 nm, such QDOT® 705 or QDOT® 800 or QDOT® ITK™ 705 or 800 quantum dots. In other variations exemplary layer structures can be monolayers of cadmium mixed with selenium or tellurium, by way of example. Nanoparticles can also be embedded in layers made from polydimethylsiloxane (PDMS), photoresist materials, such as epoxy based SU-8, cadmium, selenium, tellurium, and zinc sulfide, and combinations thereof.

As shown in simplified schematic FIG. 2A, external light source 22 travels through microlens 50 to a distance "L" within housing 54 and at distance "L" is absorbed by second layer 72, which in response, emits second wavelength ($D_2$) (78). In FIG. 2B, as deflectable membrane 60 translates in response to a pressure increase in surrounding environment 62, array structure 66 likewise translates upwards towards the first end 52 of housing 54 and moves closer towards microlens 50. As such, when external light source 22 travels distance "L" within housing 54, it now is predominantly absorbed by first layer 70, and thus emits first wavelength ($D_1$)(76).

Thus, external light source 22 is transmitted through the microlens 50 to the array structure 66. In response, array structure 66 emits wavelength 32 (which includes first wavelength ($D_1$) of emitted light 76 and/or second wavelength ($D_2$) of emitted light 78) through the microlens 50 externally to a spectrometer 80 operable to detect light energy at the first and second wavelengths. As illustrated in FIG. 2A, when the deflectable membrane 60 is not deflected the array structure 66 emits wavelengths from the top second layer 72. When the deflectable membrane 60 deflects, the array structure 66 moves closer to the microlens 50 and emits wavelengths from lower first layer 70.

While FIGS. 2A and 2B are simplified to illustrate the operational principles of microsensor device 20, the emitted first and second wavelengths of light 76, 78 from first and second layers 70, 72 may combine at different ratios to form combined emitted light 32 that is detected by spectrometer 30. In this manner, emitted light 32 represents an amount of deflection of deflectable membrane 60 (and thus of translation of array structure 66 within housing 54 to emit different ratios of first and second wavelengths) and thus represent pressure changes in the surrounding environment. In certain aspects, it is preferred that combined emitted light 32 has a wavelength at a near infrared region (NIR) having a wavelength of about 700 nm to about 900 nm.

In another variation as shown in FIGS. 3A-3C, an implantable microsensor device 20a is used with a monitoring system 24 of FIG. 1 in the same manner as the embodiment described above to internally monitor pressure of a patient 12. The microsensor device 20a comprises a tunable microlens 80 on a first side 52 of a housing 54. A second diametrically opposite side 56 of the housing 54 includes a deflectable membrane 60, which is responsive to any changes in pressure of a surrounding environment 62 within the patient 12. The housing 54 further includes walls 63, which extend from first side 52 to second side 56 to enclose the microsensor device 20a to prevent any fluid communication with the external surrounding environment 62.

The housing 54 optionally further comprises a fluid 53 that is transmissive to external light source 22 (and emitted light 32, which will be described in more detail below). The materials and dimensions of housing 54 are the same as those described above for microsensor device 20. The deflectable membrane 60 is constructed of the same material in microsensor device 20 of FIGS. 2A-2C and operates in the same manner, in that it is responsive to pressure changes in an external surrounding environment (e.g., 62). In FIG. 3A, deflectable membrane 60 is in a non-deflected state, where a pressure of surrounding environment 62 is at a first predetermined steady state level and the deflectable membrane 60 is relatively flat. Upon an increase in pressure of surrounding environment 62 as shown in FIG. 3B to as second pressure, deflectable membrane 62 translates in a direction toward first end 52 of housing 54 by upward deflection. As appreciated by those of skill in the art, while not shown, the translation or movement of deflectable lens may also be in the opposite direction if pressure falls in the surrounding environment 62.

An array structure 90 is disposed within housing 54 located between tunable microlens 80 and deflectable membrane 60. The array structure 90 is configured to receive external light source 22 which is transmitted through tunable microlens 80. In the embodiment of FIGS. 3A-3C, the array structure 90 is disposed at a fixed position within the housing 54, for example, by coupling it to the housing walls 63.

Tunable microlens 80 is formed of a flexible material. When the deflectable membrane 60 deflects, the microlens 80 changes focal lengths and/or focal angles. Thus, where deflectable membrane 60 is deflected or translates a distance "x" based on pressure changes in surrounding environment 62; tunable microlens 80 likewise is deflected upwards proportionally a distance "y." Thus, when the external surrounding environment is at a first predetermined pressure, deflectable membrane 60 is relatively flat and not deflected, so that tunable microlens 80 is likewise in a flat or non-deflected state. Thus, external light source 22 passes through tunable microlens 80 in a relatively linear pathway (arrows 92) and through the fluid medium 63. In this circumstance, external light source 22 is not directed at or absorbed by array structure 901 as reflected by the emitted wavelength (in FIG. 3A inset) being zero (0). However, when a pressure of surrounding environment 62 changes, deflectable membrane 60 experiences a proportional change in pressure (designated by $x_1$ in FIG. 3B or $x_2$ in FIG. 3C).

The fluid medium 63 inside housing 54 is biased towards first side 52 to force microlens 80 to deflect and translate in the same direction by a proportional distance $y_1$ in FIG. 3B or $y_2$ in FIG. 3C. Thus, as tunable microlens 80 is translated by distance "y," the focal angle and length of the tunable microlens 80 changes so that external light source 22 is directed to and absorbed by array structure 90. As a pressure of surrounding environment 62 becomes relatively greater, deflectable membrane 60 is further deflected upwards (FIG. 3C—$x_2$) towards first end 52, so that the tunable microlens 80 is translated or moved further upwards ($y_2$), further altering the focal angle and distance to change the location on the array structure 90 that absorbs external light source 22.

In this embodiment, tunable microlens 80 is formed from a relatively flexible and elastomeric material, such as polyparaxylylene (parylene), silicone, hydrogels, nitrides, oxides, carbides, silicides, polymethylsiloxane (PDMS), biocompatible materials, biodegradable materials, and the like. Any of the coatings 57 discussed above for the embodiment of FIGS. 2A-2C may be used to coat the tunable microlens 80, as well. In certain variations, the tunable microlens 80 is formed from PMDS and coated with parylene.

Array structure 90 includes a plurality of distinct layers 94 configured to emit a range of wavelengths. Each distinct layer 94 is has emits a distinct wavelength of light transmissive through the surrounding tissue in response to receiving external light source 22. As shown, array structure 90 includes a first layer 96 that comprises a first nanoparticle, such as a first quantum dot material, that emits light at a first wavelength in response to external light source 22. Array structure 90 further includes a second layer 98 that comprises a second nanoparticle that emits light at a second wavelength in response to external light source 22; a third layer 100 that emits light at a third wavelength in response to external light source 22; and a fourth layer 102 that emits light at a fourth wavelength in response to external light source 22. Each distinct layer (first layer 96, second layer 98, third layer 100, and fourth layer 102) comprises a nanoparticle, such as a quantum dot material array, which emits light at a different, distinct wavelength. In this way, as the focal angle and length of tunable microlens 80 is absorbed by different regions of array structure 90, a wavelength of emitted light energy 32 is altered. The wavelength of emitted light 32 can be correlated to the amount of deflection of the deflectable membrane 60 and tunable microlens 80, such that a pressure of the surrounding environment 62 can be readily determined via detection by spectrometer 30 (FIG. 1). In certain aspects, it is preferred that combined emitted light 32 has a wavelength at a near infrared region (NIR) having a wavelength of great than or equal to about 700 nm to less than or equal to about 900 nm.

Each layer 94 (e.g., first, second, third, and fourth layers 96, 98, 100, 102) can be fabricated as a quantum dot array that emits a different wavelength in the near infrared (NIR) region from about 700 nm to about 900 nm. For example, suitable nanoparticle materials are independently selected from the nanoparticle quantum dot materials discussed above in the context of first and second layer nanoparticles (70,72) for FIGS. 2A-2C. In certain variations, the plurality of distinct layers 94 can be fabricated to emit different wavelengths such as, 700 nm, 705 nm, 740 nm, 780 nm, 800 nm, 820 nm, 860 nm and 900 nm in response to external light source 22. As appreciated by those of skill in the art, the quantum dot array of each layer 94 may comprise a plurality of distinct nanoparticle materials that combine together to form a tailored wavelength emission. Additionally, each respective layer 94 may comprise a plurality of materials that emit the same or different wavelengths of light responsive to external light source 22.

As appreciated by those of skill in the art, the array structure 90 may comprise a plurality of layers 94, in addition to the first, second, third, and fourth layers 96, 98, 100, and 102, in any configuration or sequence. Optional interstitial spacing layers 106, similar to interstitial spacing layer 74 of array structure 66, are optionally disposed beneath each of first layer 96, second layer 98, third layer 100, and fourth layer 102. The wavelength of emitted light 32 (see for example, $D_1$ of inset of FIG. 3B reflecting a second pressure of external environment 62 or $D_2$ of inset of FIG. 3C reflecting a third pressure of external environment) is generated when external light source 22 reaches the respective layers 94 and thus generates a combined emitted light 32, which passes through tunable microlens 80 through the surrounding environment 62 for detection (for example, as shown in FIG. 1, brain 10, dura matter 40, skull bone 42, and scalp/skin 44 to spectrometer 30).

In certain aspects, the microsensor devices of the present disclosure are compatible with various medical imaging devices, such as MRI, CT, and ultrasound. The microsensor devices of the present disclosure can be fabricated using micro-electromechanical system (MEMS) technology, which allows for creating a flexible device that is small, accurate, durable, and biocompatible to changes in body chemistry, biology or external pressure. The microsensor devices are passive, without any internal circuitry, wireless, and relay internal pressure information externally without the need of an internal or externally connected power supply to perform.

In other aspects, the present disclosure pertains to an implantable microsensor for monitoring pressure in a patient comprising a microlens, a deflectable membrane responsive to a change in pressure of a surrounding environment within the patient, and an array structure disposed between the microlens and the deflectable membrane. The array structure comprises a first layer including a first nanoparticle that emits a first wavelength of light responsive to an external light source and a second layer including a second nanoparticle that emits a second wavelength of light responsive to the external light source. The first wavelength of light and the second wavelength of light are respectively transmissive through the surrounding environment and distinct from one another. Either the array structure or the microlens translates with the deflectable membrane in response to the change in pressure of the surrounding environment.

In yet other aspects, the present disclosure provides an implantable microsensor for monitoring intracranial or intraocular pressure in a patient. The microsensor device comprises a microlens, a deflectable membrane responsive to a change in internal pressure of a brain or an eye of a patient, and an array structure disposed between the microlens and the deflectable membrane. The array structure emits a light representative of the internal intracranial pressure or an intraocular pressure at a near infrared region (NIR) having a wavelength of about 700 nm to about 900 nm. The array structure comprises a first layer including a first nanoparticle that emits a first wavelength of light responsive to an external light source and a second layer including a second nanoparticle that emits a second wavelength of light responsive to the external light source. Either the array structure or the microlens translates with the deflectable membrane in response to the change in pressure of the surrounding environment. The microsensor device is compatible with imaging devices.

It is contemplated that the microsensor devices of the present disclosure, which lack electronic/metal components, can be formed of fully biodegradable materials. This permits the implantable microsensor to be used for a certain predetermined period of time and then to be resorbed or degraded in vivo. Biodegradable materials suitable for use in the microsensor devices include by way of non-limiting example, cross-linked proteins such as human albumin, fibrin gels, polysaccharides such as starch or agarose, poly (DL-lactide) and poly (DL-glycolide), polyanhydrides, fatty acid/cholesterol mixtures that form semi-solid derivates, hyaluronates and liquid crystals of monooliein, water, and the like.

The foregoing description of the embodiments has been provided for purposes of illustration and description. It is not intended to be exhaustive or to limit the invention. Individual elements or features of a particular embodiment are generally not limited to that particular embodiment, but, where appli-

What is claimed is:

1. A method for internally monitoring pressure of a patient, the method comprising:
transmitting an external light source through tissue of the patient to a passive microsensor device operable to optically encode internal pressure changes within the patient without an internal power supply, an external power supply, an internal current, an external current, an internal impedance, or an external impedance, wherein in response to receiving said transmitted light, said passive microsensor device emits light representative of said internal pressure at a near infrared region (NIR) wavelength, wherein said passive microsensor device comprises a housing sealed to prevent fluid communication with a surrounding environment, said housing comprising:
a microlens;
a deflectable membrane responsive to a change in pressure of said surrounding environment within the patient:
an array structure disposed within said housing between said microlens and said deflectable membrane that emits said light representative of said internal pressure at said near infrared region (NIR) wavelength without an internal power supply, an external power supply, an internal current, an external current, an internal impedance, or an external impedance, wherein said array structure comprises a first layer including a first nanoparticle that emits a first wavelength of light responsive to an external light source and a second layer including a second nanoparticle that emits a second wavelength of light responsive to said external light source; wherein said first wavelength of light and said second wavelength of light are distinct from one another;
wherein either said array structure or said microlens translates with said deflectable membrane in response to said change in pressure of said surrounding environment; and
detecting said emitted light with a spectrometer.

2. The method of claim 1, wherein said passive microsensor device is implanted in an organ selected from the group consisting of: a brain, an eye, and a blood vessel.

3. The method of claim 1, wherein a change in internal pressure relates to a change in a wavelength of emitted light.

4. The method of claim 1, wherein said passive microsensor device is compatible with imaging devices.

5. An implantable microsensor for passively monitoring pressure in a patient comprising:
a microlens;
a deflectable membrane responsive to a change in pressure of a surrounding environment within the patient; and
an array structure disposed between said microlens and said deflectable membrane, said array structure comprising a first layer including a first nanoparticle that emits a first wavelength of light responsive to an external light source and a second layer including a second nanoparticle that emits a second wavelength of light responsive to said external light source wherein said array structure emits said first wavelength of light and said second wavelength of light without an internal power supply, an external power supply, an internal current, an external current, an internal impedance, or an external impedance; wherein said first wavelength of light and said second wavelength of light are respectively transmissive through said surrounding environment and distinct from one another;
wherein either said array structure or said microlens translates with said deflectable membrane in response to said change in pressure of said surrounding environment.

6. The implantable microsensor of claim 5, wherein the implantable microsensor device is implanted in an organ of the patient selected from the group consisting of: a brain, an eye, and a blood vessel and is further compatible with medical imaging devices.

7. The implantable microsensor of claim 5, further comprising a housing comprising said microlens and said deflectable membrane and wherein said array structure is disposed therein, wherein said housing further comprises a fluid that is transmissive to said external light source.

8. The implantable microsensor of claim 7 wherein said housing has a major dimension ranging from greater than or equal to 30 µm to less than or equal to about 3 mm.

9. The implantable microsensor of claim 5 wherein said array structure comprises a plurality of distinct layers including at least said first layer and said second layer and a third layer, wherein said plurality of distinct layers is configured to emit a range of wavelengths, wherein said wavelengths are near infrared (NIR).

10. The implantable microsensor of claim 9 wherein said first layer is configured to emit a wavelength at about 705 nm.

11. The implantable microsensor of claim 9 wherein said second layer is configured to emit a wavelength at about 800 nm.

12. The implantable microsensor of claim 9 wherein said first layer and said second layer nanoparticles independently comprise a nanoparticle compound including an element selected from the group consisting of: cadmium, indium, selenium, tellurium, zinc, sulfur, phosphorus, and combinations thereof.

13. The implantable microsensor of claim 5 wherein said external light source is near infrared (NIR) ranging from greater than or equal to about 650 nm to less than or equal to about 850 nm.

14. The implantable microsensor of claim 5 wherein said microlens translates with said deflectable membrane in response to said change in pressure of said surrounding environment.

15. The implantable microsensor of claim 14 wherein said microlens comprises a tunable lens, wherein said tunable lens comprises a deflectable material selected from the group consisting of: a polysiloxane elastomer, polydimethylsiloxane (PDMS) elastomer, a photoresist material, polyxylylene and its derivatives, and combinations thereof.

16. The implantable microsensor of claim 5 wherein said array structure translates with said deflectable membrane in response to said change in pressure of said surrounding environment.

17. The implantable microsensor of claim 16 wherein said microlens comprises a rigid material selected from the group consisting of: silicon oxides, silicon dioxide, polysiloxane materials, polydimethylsiloxane (PDMS), photoresist materials, polycarbonates, acrylic polymers and derivatives thereof, polymethylmethacrylate (PMMA), optical adhesives, and combinations thereof.

18. The implantable microsensor of claim 5 which is capable of detecting said change in pressure at a range of about −20 mm Hg to about 300 mm Hg.

19. The implantable microsensor of claim 5 wherein said external light source is transmitted through said microlens to said array structure and said microlens transmits said first wavelength of emitted light and/or said second wavelength of emitted light externally to a spectrometer operable to detect light energy at said first and second wavelengths.

20. An implantable microsensor for passively monitoring intracranial or intraocular pressure in a patient comprising:
   a housing sealed to prevent fluid communication with a surrounding environment, said housing comprising:
   a microlens;
   a deflectable membrane responsive to a change in internal pressure of a brain or an eye of a patient ranging from greater than or equal to about −20 mm Hg to less than or equal to about 300 mm Hg;
   a passive array structure disposed between said microlens and said deflectable membrane within said housing, said passive array structure emitting a light representative of said internal intracranial pressure or said intraocular pressure at a near infrared region (NIR) having wavelength without an internal power supply, an external power supply, an internal current, an external current, an internal impedance, or an external impedance, wherein said passive array structure comprises a first layer including a first nanoparticle that emits a first wavelength of light responsive to an external light source and a second layer including a second nanoparticle that emits a second wavelength of light responsive to said external light source;
   wherein said passive array structure translates with said deflectable membrane in response to said change in pressure of said surrounding environment; and
   wherein the implantable microsensor is compatible with medical imaging devices.

21. The implantable microsensor of claim 20 which is capable of detecting said change in intracranial pressure or intraocular pressure at a range of greater than or equal to about −10 mm Hg to less than or equal to about 60 mm Hg.

* * * * *